(12) United States Patent
Danziger

(10) Patent No.: US 9,736,998 B2
(45) Date of Patent: Aug. 22, 2017

(54) OTOMERIA PLANTS

(71) Applicant: Danziger Dan Flower Farm, Moshav Mishmar HaShiva (IL)

(72) Inventor: Gavriel Danziger, Moshav Nir-Zvi (IL)

(73) Assignee: Danziger Dan Flower Farm, Moshav Mishmar HaShiva (IL)

( * ) Notice: Subject to any disclaimer, the term of this patent is extended or adjusted under 35 U.S.C. 154(b) by 493 days.

(21) Appl. No.: 14/359,979

(22) PCT Filed: Nov. 22, 2012

(86) PCT No.: PCT/IL2012/050476
§ 371 (c)(1),
(2) Date: May 22, 2014

(87) PCT Pub. No.: WO2013/076729
PCT Pub. Date: May 30, 2013

(65) Prior Publication Data
US 2014/0317772 A1  Oct. 23, 2014

Related U.S. Application Data

(60) Provisional application No. 61/643,992, filed on May 8, 2012, provisional application No. 61/582,510, filed on Jan. 3, 2012, provisional application No. 61/563,105, filed on Nov. 23, 2011.

(51) Int. Cl.
*A01H 5/02* (2006.01)
*C12N 5/00* (2006.01)

(52) U.S. Cl.
CPC ............. *A01H 5/02* (2013.01); *C12N 5/0025* (2013.01)

(58) Field of Classification Search
None
See application file for complete search history.

(56) References Cited

FOREIGN PATENT DOCUMENTS

| JP | 2006-050960 | 2/2006 |
|---|---|---|
| WO | WO 97/17429 | 5/1997 |
| WO | WO 2013/076729 | 5/2013 |

OTHER PUBLICATIONS

Horn 2002 Breeding Methods and Breeding Research in Breeding for Ornamentals: Classical and Molecular Approaches, pp. 47-83.*
Karehed et al 2007, Taxon 56(4): 1051-1076.*
Winter 2005 Mississippi State University Extension.*
International Serch Report and the Written Opinion Dated Mar. 20, 2013 From the International Searching Authority Re. Application No. PCT/IL2012/050476.
Danziger "Dan" Flower "Otomeria. A How-to Production Guide", Greenhouse Management, 1 P., Sep. 2011.
Dessein et al. "Pollen Morphological Survey of Pentas (Rubiaceae-Rubioideae) and Its Closest Allies", Review of Palaeobotany and Palynology, 112(4):189-205, Nov. 1, 2000.
Royal Botanic Gardens "Specimen Image K000414233—Otomeria Eliator", Database Herbarium Catalogue [Online], Greenhouse Management, Royal Botanic Gardens Kew, Database Accession No. K000414233, 1 P., Nov. 1888.
Royal Botanical Gardens "Specimen Details—K000043352— Otomeria Cameronica (Bremek.) Hepper", Database Herbarium Catalogue [Online], Royal Botanical Gardens Kew, Database Accession No. K000043352, 1 P., Mar. 26, 1964.
Trial Gardens "Danziger Flower Farm: Noa™ Red Wine NEW, Noa™ Sunrise NEW, Noa™ Sunset NEW, Noa™ Ultra Purple, O'premiera White NEW", Penn State Horticultural Trial Gardens, 2011.
Trial Gardens "Danziger Flower Farm: O'premiera™ Baby Pink NEW, O'premiera™ Pink NEW, O'premiera™ Ruby NEW, Ostica™ Blue Eye, Ostica™ Lemon", Penn State Horticultural Trial Gardens, 2011.
UGA "Otomeria O'Premiera Baby Pink", Danziger Flower Farm, The Trial Gardens at UGA, 2011.
UGA "Otomeria O'Premiera Ruby", Danziger Flower Farm, The Trial Gardens at UGA, 2011.
UGA "Otomeria O'Premiera White", Danziger Flower Farm, The Trial Gardens at UGA, 2011.
Verdcourt "Flora Zambesiaca", Royal Botanical Gardens Kew, 2 P., 1989.
International Preliminary Report on Patentability Dated Jun. 5, 2014 From the International Bureau of WIPO Re. Application No. PCT/IL2012/050476.

* cited by examiner

*Primary Examiner* — David H Kruse

(57) ABSTRACT

Novel Otomeria plants are provided herein. Also provided are methods and systems for generating such plants and tissues for use in such methods and systems.

4 Claims, 4 Drawing Sheets
(4 of 4 Drawing Sheet(s) Filed in Color)

US 9,736,998 B2

OTOMERIA PLANTS

RELATED APPLICATIONS

This application is a National Phase of PCT Patent Application No. PCT/IL2012/050476 having International filing date of Nov. 22, 2012, which claims the benefit of priority under 35 USC §119(e) of U.S. Provisional Patent Application Nos. 61/643,992 filed on May 8, 2012, 61/582,510 filed on Jan. 3, 2012 and 61/563,105 filed on Nov. 23, 2011. The contents of the above applications are all incorporated by reference as if fully set forth herein in their entirety.

FIELD AND BACKGROUND OF THE INVENTION

The present invention relates to new and distinctive *Otomeria* plants and, more particularly to *Otomeria* plants having commercially valuable ornamental traits. The present invention also relates to methods and systems for generating such plants.

The ornamental plant market is saturated with traditional plants and flowers with demand for new ornamental varieties being constantly on the rise in both the cut flowers and potted plant markets.

*Otomeria* is a member of the Rubiaceae family. The genus includes twenty-one known species of annual or perennial herbs originating from East Africa and Madagascar. Very little is known about the genus and its breeding and as such, none of the *Otomeria* species are commercially cultivated as ornamental plants.

The species *Otomeria oculata* is an herb with many erect, non branched stems and ovate, lanceolate leaves. The pink or sometimes white corolla is 18-32 mm long and has a dark center. The tube is narrow and cylindrical and the spreading lobes are 5-10 mm long. This species is a heterostylous, with two types of flowers—a "Female type" flower characterized by short stamens and a long pistil with two-lobed stigma, visible above the petals (termed—pin flower) and a "Male type" flower characterized by a short pistil and long stamens visible above the petals (termed—thrum flower). The ovary of *Otomeria oculata* is inferior and located on the flowering stalk.

This species is uncommon and found in dry rocky grassland at altitudes of 530-1,650 m (Vuilleumier, B. S., 1967. The Origin and Evolutionary Development of Heterostyly in the Angiosperms. Evolution 21, 2: 210-226.; Blundell, M., 1982. The Wild Flowers of Kenya. p.: 75. Collins, St. James's Place, London).

*Otomeria* species such as *Otomeria oculata* have little or no commercial value to the flower industry due to a lack of a breeding program and ornamentally-valuable traits.

SUMMARY OF THE INVENTION

According to an aspect of some embodiments of the present invention there is provided a cultivated *Otomeria* plant characterized by red, pink or pure-white flowers.

According to an aspect of some embodiments of the present invention there is provided a cultivated *Otomeria* plant having flowers characterized by higher Peonidin-hex-deoxyhexose or Malvidin-hex-deoxyhexose values than that found in wild type *Otomeria oculata*.

According to an aspect of some embodiments of the present invention there is provided a cultivated *Otomeria* plant having flowers characterized by lower Peonidin-hex-deoxyhexose and/or Malvidin-hex-deoxyhexose values than that found in the flower of cultivated *Otomeria oculata*.

According to an aspect of some embodiments of the present invention there is provided a cultivated *Otomeria* plant characterized by red, pink or pure-white flowers, wherein a sample of representative seeds of an *Otomeria* plant characterized by red, pink or pure-white flowers is selected from the group consisting of OT-7-70, OT-7-93, OT-7-129, OT-7-139, OT-7-141, OT-7-154, OT-7-155, OT-7-163, OT-7-164, OT-7-267, OT-9-430, OT-9-432, OT-9-433, OT-9-434, OT-8-300, OT-8-301, OT-8-302, OT-8-303, OT-8-304, OT-8-305, OT-8-306, OT-8-307, OT-8-308, OT-8-309, OT-8-310, OT-8-311, OT-8-336, OT-8-337, OT-8-338, OT-8-340, OT-8-344, OT-8-361, OT-8-364, OT-8-365, OT-8-369, OT-8-381, OT-8-382, OT-8-383, OT-8-384, OT-8-386, OT-8-387, OT-8-388, OT-6-2, OT-7-62 and OT-8-407. Representative seeds of OT-8-407 have been deposited under the Budapest Treaty in the Korean Collection for Type Cultures on Jan. 27, 2012 under KCTC 12122BP. Representative seeds of OT-7-62 have been deposited under the Budapest Treaty in the Korean Collection for Type Cultures on Jan. 27, 2012 under KCTC 12120BP. Representative seeds of OT-9-567 have been deposited under the Budapest Treaty in the Korean Collection for Type Cultures on Jan. 27, 2012 under KCTC 12123BP. Representative seeds of OT-7-139 have been deposited under the Budapest Treaty in the Korean Collection for Type Cultures on Jan. 27, 2012 under KCTC 12121BP.

According to an aspect of some embodiments of the present invention there is provided an *Otomeria* plant or part thereof characterized by red, pink or pure-white flowers, wherein a sample of representative seeds of the *Otomeria* plant is selected from the group consisting of OT-7-70, OT-7-93, OT-7-129, OT-7-139, OT-7-141, OT-7-154, OT-7-155, OT-7-163, OT-7-164, OT-7-267, OT-9-430, OT-9-432, OT-9-433, OT-9-434, OT-8-300, OT-8-301, OT-8-302, OT-8-303, OT-8-304, OT-8-305, OT-8-306, OT-8-307, OT-8-308, OT-8-309, OT-8-310, OT-8-311, OT-8-336, OT-8-337, OT-8-338, OT-8-340 OT-8-344, OT-8-361, OT-8-364, OT-8-365, OT-8-369, OT-8-381, OT-8-382, OT-8-383, OT-8-384, OT-8-386, OT-8-387, OT-8-388, OT-6-2, OT-7-62 and OT-8-407. Representative seeds of OT-8-407 have been deposited under the Budapest Treaty in the Korean Collection for Type Cultures on Jan. 27, 2012 under KCTC 12122BP. Representative seeds of OT-7-62 have been deposited under the Budapest Treaty in the Korean Collection for Type Cultures on Jan. 27, 2012 under KCTC 12120BP. Representative seeds of OT-9-567 have been deposited under the Budapest Treaty in the Korean Collection for Type Cultures on Jan. 27, 2012 under KCTC 12123BP. Representative seeds of OT-7-139 have been deposited under the Budapest Treaty in the Korean Collection for Type Cultures on Jan. 27, 2012 under KCTC 12121BP.

According to an aspect of some embodiments of the present invention there is provided a polyploid *Otomeria* plant having a higher chromosome number than that found in *Otomeria oculata*.

According to some embodiments of the invention, the plant has white flowers or dark pink flowers.

According to some embodiments of the invention, the pure white flowers are without a colored distinguishable center.

According to some embodiments of the invention, a sample of representative seeds of the *Otomeria* plant characterized by red, pink or pure-white flowers is selected from the group consisting of OT-7-70, OT-7-93, OT-7-129, OT-7-139, OT-7-141, OT-7-154, OT-7-155, OT-7-163, OT-7-164, OT-7-267, OT-9-430, OT-9-432, OT-9-433, OT-9-434, OT-8-300, OT-8-301, OT-8-302, OT-8-303, OT-8-304, OT-8-305, OT-8-306, OT-8-307, OT-8-308, OT-8-309, OT-8-310, OT-8-311, OT-8-336, OT-8-337, OT-8-338, OT-8-340, OT-8-344, OT-8-361, OT-8-364, OT-8-365, OT-8-369, OT-8-381, OT-8-382, OT-8-383, OT-8-384, OT-8-386, OT-8-387, OT-8-388, OT-6-2, OT-7-62 and OT-8-407. Representative seeds of OT-8-407 have been deposited under the Budapest Treaty in the Korean Collection for Type Cultures on Jan. 27, 2012 under KCTC 12122BP. Representative seeds of OT-7-62 have been deposited under the Budapest Treaty in the Korean Collection for Type Cultures on Jan. 27, 2012 under KCTC 12120BP. Representative seeds of OT-9-567 have been deposited under the Budapest Treaty in the Korean Collection for Type Cultures on Jan. 27, 2012 under KCTC 12123BP. Representative seeds of OT-7-139 have been deposited under the Budapest Treaty in the Korean Collection for Type Cultures on Jan. 27, 2012 under KCTC 12121BP.

According to an aspect of some embodiments of the present invention there is provided a plant having as a parental ancestor the plant described herein.

According to some embodiments of the invention, the plant is an inbred.

According to some embodiments of the invention, the plant is a cross-bred.

According to an aspect of some embodiments of the present invention there is provided a planted field comprising the plant as described herein.

According to an aspect of some embodiments of the present invention there is provided a plant part of the plant as described herein.

According to some embodiments of the invention, the plant part is a seed.

According to some embodiments of the invention, the plant as described herein has a trait selected from the group consisting of compact and branched habit, floriferous and continuous flowering.

According to some embodiments of the invention, the plant is non-transgenic.

According to an aspect of some embodiments of the present invention there is provided a tissue culture of cells produced from the plant as described herein or part thereof.

According to some embodiments of the invention, the tissue culture regenerates plants capable of expressing all the morphological and physiological characteristics of the *Otomeria* plant.

According to some embodiments of the invention, the tissue culture is regenerated from cells or protoplasts of a tissue selected from the group consisting of seeds, leaves, stems, pollens, roots, root tips, anthers, ovules, petals, flowers and embryos.

According to an aspect of some embodiments of the present invention there is provided a method of developing a cultivated plant using plant breeding techniques, the method comprising using the plant described herein as a source of breeding material for self-breeding and/or cross-breeding.

According to an aspect of some embodiments of the present invention there is provided a method of developing a *Otomeria* plant using plant breeding techniques which employ an *Otomeria* plant, or its parts, as a source of plant breeding material, the method comprising utilizing a polyploid *Otomeria* plant having a higher chromosome number than that found in *Otomeria oculata*, as a source of breeding material.

According to an aspect of some embodiments of the present invention there is provided a method of developing the *Otomeria* plant, the method comprising:

(i) subjecting a cultivated *Otomeria oculata* to open of self-pollination so as to obtain hybrid seeds; and (ii) growing plants of the hybrid seeds; and (iii) selecting a plant of the plants that exhibits a red, white or dark-pink flower color.

According to some embodiments of the invention, the plant breeding techniques are selected from the group consisting of recurrent selection, backcrossing, pedigree breeding, restriction fragment length polymorphism enhanced selection, genetic marker enhanced selection, and transformation.

According to an aspect of some embodiments of the present invention there is provided a system for developing an *Otomeria* plant using plant breeding techniques, the system comprising a polyploidy *Otomeria* plant or parts thereof as a source of the breeding material, wherein said polyploid *Otomeria* plant or parts thereof have a higher chromosome number than that found in *Otomeria oculata*.

According to an aspect of some embodiments of the present invention there is provided a method of developing the *Otomeria* plant described herein, the method comprising:

(i) subjecting a cultivated *Otomeria oculata* to open of self-pollination so as to obtain hybrid seeds; and (ii) growing plants of the hybrid seeds; and (iii) selecting a plant of the plants that exhibits a higher or lower Peonidin-hex-deoxyhexose or Malvidin-hex-deoxyhexose value as compared to *Otomeria oculata* or a cultivar thereof.

According to an aspect of some embodiments of the present invention there is provided a cultivated *Otomeria* plant.

According to an aspect of some embodiments of the present invention there is provided a cultivated *Otomeria* plant for which representative seeds have been deposited under the Budapest Treaty in the Korean Collection for Type Cultures under KCTC 12122BP (OT-8-407).

According to an aspect of some embodiments of the present invention there is provided a cultivated *Otomeria* plant for which representative seeds have been deposited under the Budapest Treaty in the Korean Collection for Type Cultures under KCTC 12120BP (OT-7-62).

According to an aspect of some embodiments of the present invention there is provided a cultivated *Otomeria* plant for which representative seeds have been deposited under the Budapest Treaty in the Korean Collection for Type Cultures under KCTC 12123BP (OT-9-567).

According to an aspect of some embodiments of the present invention there is provided a cultivated *Otomeria* plant for which representative seeds have been deposited under the Budapest Treaty in the Korean Collection for Type Cultures under KCTC 12121BP (OT-7-139).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an image of a cultivated *Otomeria* plant with light-pink flowers (7-62). Color according to RHS (2001): Violet 84C with dark center Red-Purple 59-A.

FIG. 2 is an image of a cultivated *Otomeria* plant with dark-pink flowers (line 8-407). Color according to RHS (2001): Purple 77-B with a dark center Red-Purple 71-A.

FIG. 3 is an image of a cultivated *Otomeria* plant with white flowers (line 7-139). Color according to RHS mini color chart (2005): White 60-N999D.

FIG. 4 is an image of a cultivated *Otomeria* plant with red flowers (line 9-567). Color according to RHS (2001): Red 46-A, with dark center Red 53-A.

Figure 5A:
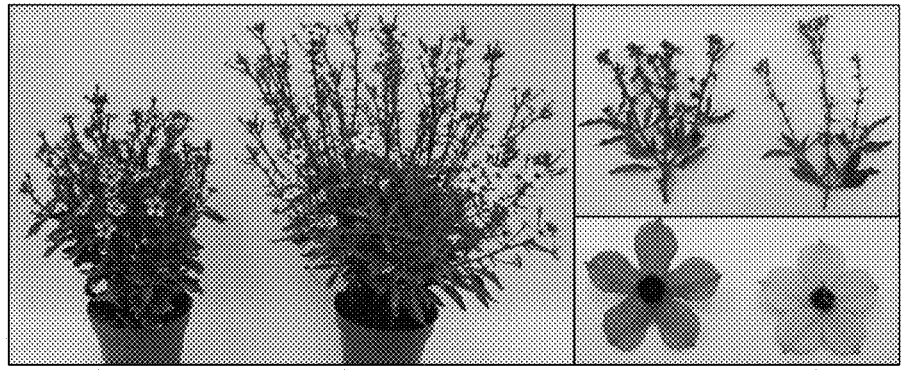
Figure 5B:
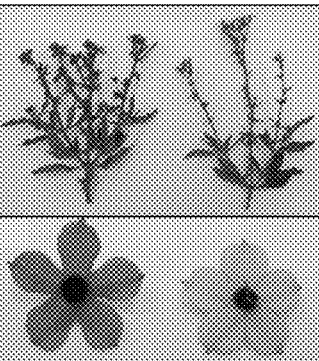
Figure 5C:
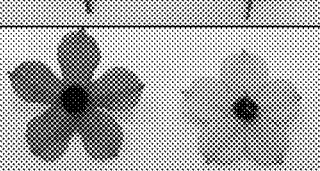

FIGS. 5A-C illustrate several *Otomeria* cultivars generated using the method of the present invention. FIG. 5A illustrates a pink flowered non-branched habit Z-9 line (right) and the dark-pink flowered, compact and branched 8-349 line (left). FIG. 5B illustrates a non-branched stem of the Z-9 line (right) and a stem of line 8-349 (left). FIG. 5C illustrates a pink flower of the Z-9 line (right) and a dark-pink flower of the 8-349 line (left).

Figure 6:
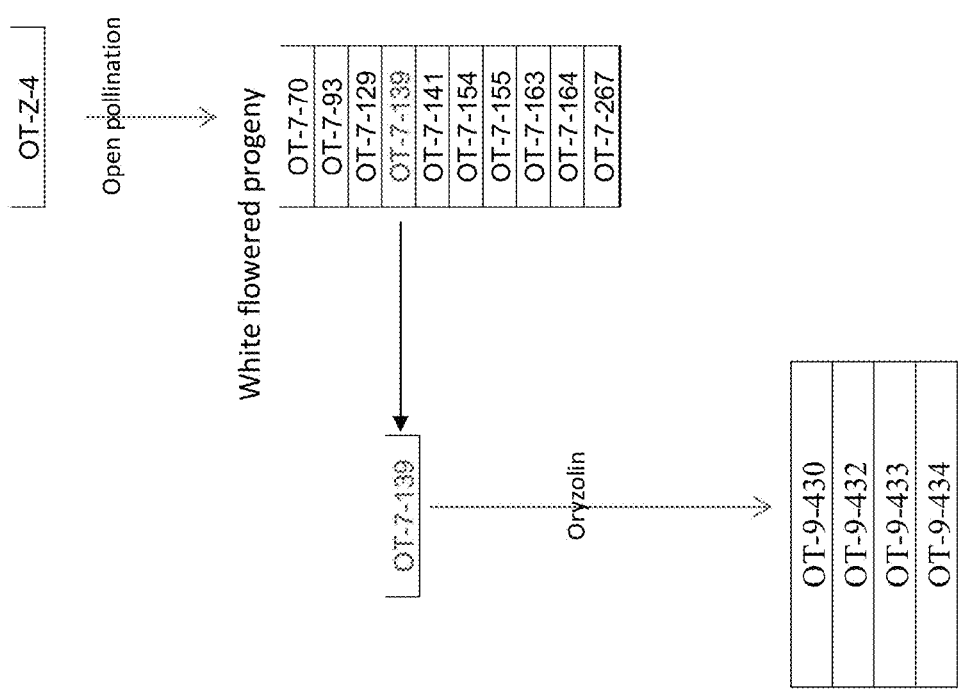

FIG. 6 is a flow chart illustrating the generation of white flowered *Otomeria* with or without a multiplied genome.

Figure 7:
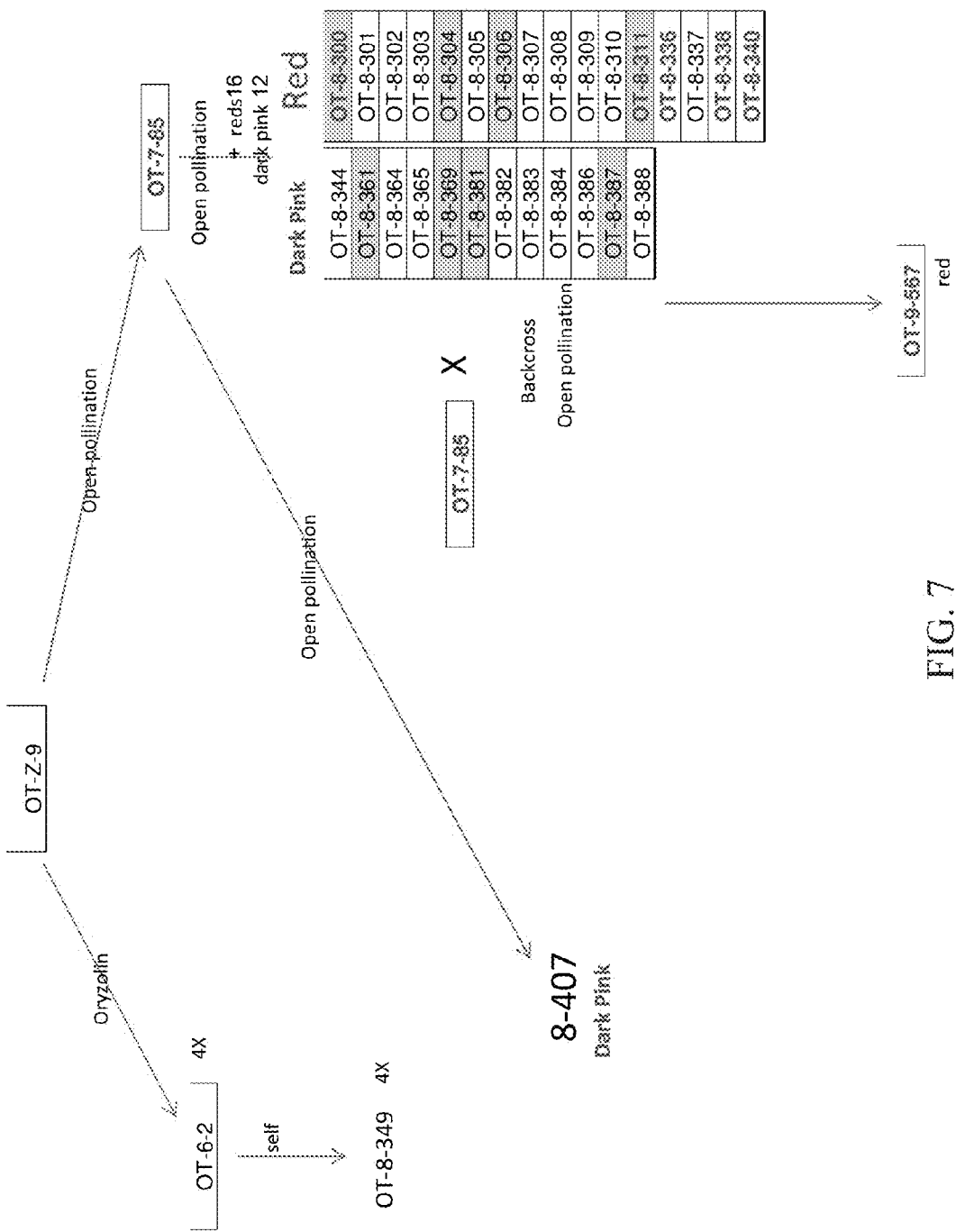

FIG. 7 is a flow chart illustrating the generation of red and dark pink *Otomerias*. Of note, FIGS. 6 and 7 illustrate independent approaches for generating novel plants according to some embodiments of the invention.

Figure 8:
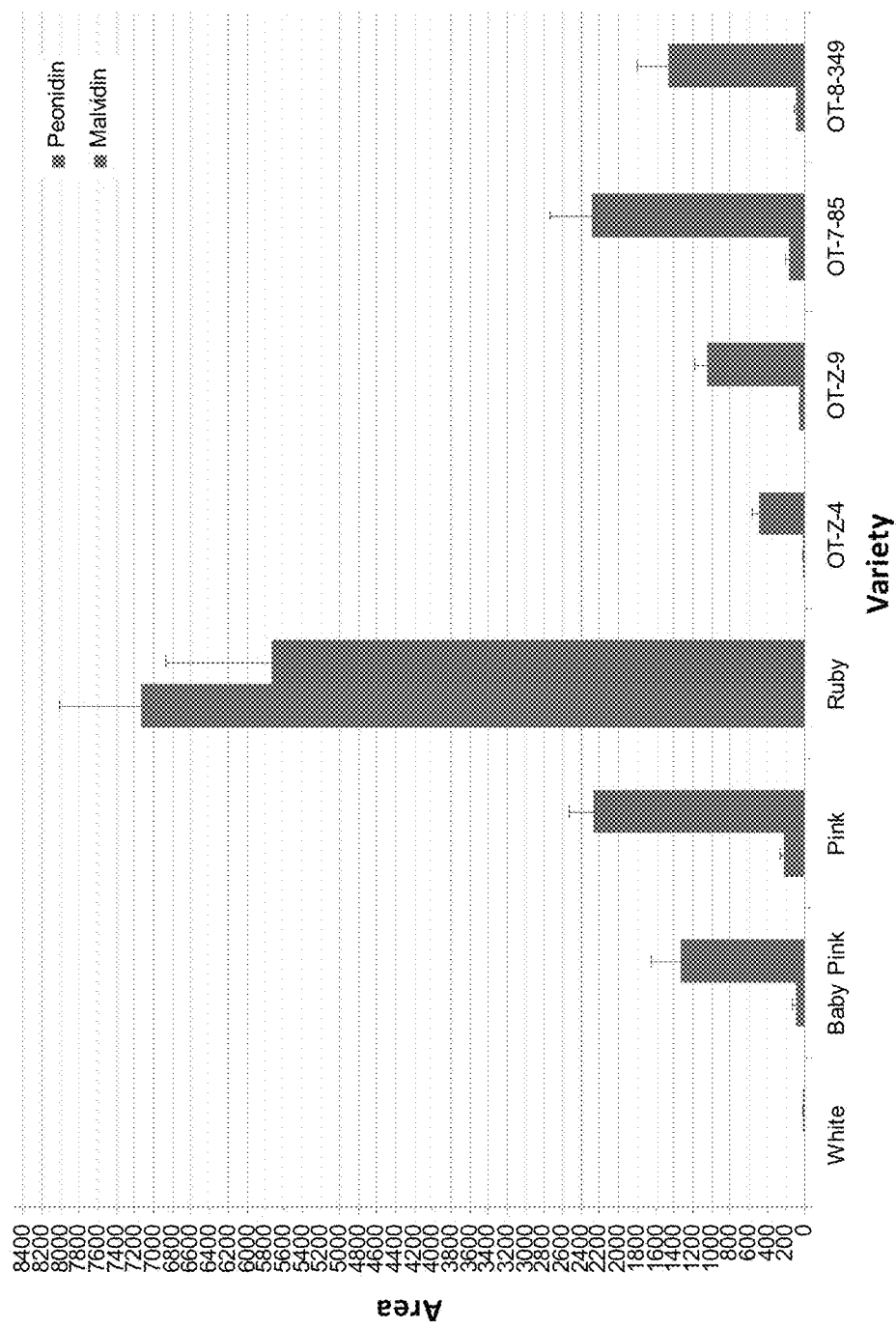

FIG. 8 is a histogram showing peonidin and malvidin values in flowers of plants of some embodiments of the invention.

DESCRIPTION OF THE PREFERRED EMBODIMENTS

The present invention is of novel *Otomeria* plants and methods of production thereof.

The principles and operation of the present invention may be better understood with reference to the accompanying drawing and descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Terminology

In the description which follows, a number of terms are used. In order to provide a clear and consistent understanding of the specification and claims, the following definitions are provided:

Line/genome/cultivar/variety—interchangeably used to refer to the genetic complement contained in the plant.

Full maturity—growth stage when *Otomeria* plants reach full bloom. At this stage, all the main branches are flowering—bearing flower buds at the tip of the flowering spike, young flowers and more mature flowers towards the lower part of the spike and seed capsules at the lowest part of the spike.

Allele—any of one or more alternative forms of a gene locus, all of which alleles relate to one trait or characteristic (e.g., allele involved in the anthocyanine pathway). In a diploid cell or organism, the two alleles of a given gene occupy corresponding loci on a pair of homologous chromosomes.

Backcrossing—process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing—the mating of two parent plants.

Cross-pollination—fertilization by the union of two gametes from different plants.

Self-pollination: The transfer of pollen from the anther to the stigma of the same plant.

Hybrid—progeny of the cross of two non-isogenic plants.

Genotype—the genetic constitution of a cell or organism.

Phenotype—the detectable characteristics of a cell or organism, which characteristics are the manifestation of gene expression.

Haploid—a cell or organism having one set of the two sets of chromosomes in a diploid.

Polyploid—a cell or organism having more than two paired (homologous) sets of chromosomes.

Linkage—a phenomenon wherein alleles on the same chromosome tend to segregate together more often than expected by chance if their transmission was independent.

Marker—a readily detectable phenotype, preferably inherited in co-dominant fashion (both alleles at a locus in a diploid heterozygote are readily detectable), with no environmental variance component, i.e., heritability of 1.

Recurrent Selection—used in breeding to increase the frequency of favorable genes by repeated cycles of selection.

Pedigree breeding—a breeding technique that is used to create entirely new varieties of plants that combine the best qualities of selected existing varieties.

Transformation—genetic alteration of a cell resulting from the direct uptake, incorporation and expression of exogenous genetic material (e.g. exogenous DNA).

Plant height—plant height is taken from the top of soil to the top node of the plant and is measured in centimeters.

Substantially equivalent—a characteristic that, when compared, does not show a statistically significant difference (e.g., $p=0.05$) from the mean.

While reducing the present invention to practice, the present inventor has cultivated an *Otomeria oculata* plant and devised an *Otomeria* breeding program which has resulted in the generation of cultivated *Otomeria* species/varieties having ornamental and growth characteristics distinguishable from those of wild *Otomeria*.

As is mentioned hereinabove and illustrated by the Examples section which follows, the present inventor has, for the first time, produced stable *Otomeria* varieties with unique flower coloring and/or commercially valuable traits such as compact, branched and floriferous and/or continuous flowering.

*Otomeria oculata* plants are typically grown in Africa and more specifically at the mountains of Ethiopia, Uganda and Kenya, from where seeds can be obtained for breeding and cultivation. The plant is well documented and described in:

appsdotkewdotorg/herbcat/getHomePageResultsdotdo-?homePageSearch Text=OTOMERIA+OCULATA&homePageSearchOption=scientific_name&nameOf SearchPage=home_page&x7&y=4

Flora of Tropical East Africa, page 1 (1976) B. Verdcour, citing the work of S. Moore on the plant. Table 1 below provides phanotypic characterization of *Otomeria oculata*.

According to an aspect of the invention there is provided a cultivated *Otomeria oculata* plant. As is described in Example 1 of the Examples section which follows, the present inventor has cultivated *Otomeria* and obtained a collection of ornamental and growth characteristics distinguishable from those of wild *Otomeria*.

Example 1 below provides phenotypic characteristics of such cultivars designated Z-4 and Z-9 (interchangeably used with OT-Z-4 and OT-Z-9, respectively).

According to an alternative embodiment, the plant of the invention is characterized by a unique anthocyanin content. See Tables 5a-b below.

According to a specific embodiment, the flower of the plant of the invention comprises a higher (e.g., ×1.5, ×2, ×5, ×10, ×15, ×20, ×50, ×100, ×150, ×200) Peonidin-hex-deoxyhexose or Malvidin-hex-deoxyhexose content as compared to that found in the flower of *Otomeria oculata* or a cultivated variety thereof (e.g., Z-4 or Z-9). See for instance Tables 5a-b OT-7-62, OT-8-407 and OT-9-567.

According to a specific embodiment, the flower of the plant of the invention comprises a non-detectable level of Peonidin-hex-deoxyhexose or Malvidin-hex-deoxyhexose as compared to that found in the flower of *Otomeria oculata* or a cultivated variety thereof (e.g., Z-4 or Z-9). See for instance Tables 5a-b OT-7-139. Non-detectable levels of Peonidin-hex-deoxyhexose are found in the white cultivar of the invention e.g., OT-7-139.

Of note, throughout the line names may be identified with "OT" initials or without.

Methods of determining anthocyanin content are described hereinbelow (e.g., UPLC-QTOF-MS).

As used herein the term "plant" refers to a whole plant or parts thereof.

The phrase "plant part" refers to plant cells or plant parts (tissues) such as from which plants can be generated, including plant protoplasts, plant cali, plant clumps, and plant cells that are intact in plants, or part of plants, such as seeds, leaves, stems, pollens, roots, root tips, anthers, ovules, petals, flowers, seedlings, embryos and bolls.

The *Otomeria* of the present invention may be a diploid or a polyploid (e.g., 4N, 6N, 8N etc.). See Example 3 below.

According to a specific embodiment, the polyploid *Otomeria* has a higher chromosome number than the wild type *Otomeria oculata* (e.g., at least one chromosome set or portions thereof) such as for example two folds greater amount of genetic material (i.e., chromosomes) as compared to the wild type plant or a cultivated variety thereof (e.g., Z-4 or Z-9) and as described in Table 4b of the Examples section which follows. Induction of polyploidy is typically performed by subjecting a plant tissue to a G2/M cycle inhibitor.

Typically, the G2/M cycle inhibitor comprises a microtubule polymerization inhibitor.

Examples of microtubule cycle inhibitors include, but are not limited to oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophosmethyl, taxol, vinblastine, griseofulvin, caffeine, bis-ANS, maytansine, vinbalstine, vinblastine sulphate and podophyllotoxin.

Induction of polyploidy can be performed on the wild-type plant, the cultivated plant (e.g., FIG. 7) or the cultivated plant that exhibits new flower color (FIG. 6), the latter is mainly done to improve horticultural traits.

As mentioned, the cultivated *Otomeria* of the present invention can be subjected to breeding program and selection of plants having *Otomeria* with novel flower coloring. Selection can be done based on anthocyanin content e.g., Peonidin-hex-deoxyhexose or Malvidin-hex-deoxyhexose.

Thus, according to an aspect of the present invention there is provided an *Otomeria* plant characterized by pink, red or pure white flowers.

As used herein the term "pink" refers to light pink color having a color range according to RHS (2001)" Purple 75-D; Red-Purple 65-D, 69-B,C; Red 56-C,D, White N 155-C,B. Typically the light pink subspecies has a dark center color according to RHS (2001): Red-Purple 59-B, 60-B, 61-A, 71-C. The 7-62 line, a representative of the subspecies, is characterized by Violet 84C with dark center Red-Purple 59-A according to RHS (2001); and dark pink color which varies according to RHS (2001): Red Purple 64-A, B; Purple N 78-B, C; Purple 70-A, B, 75-A, 77-C,D Grayed-Purple 186-C, D. Typically the dark pink subspecies has a dark center color according to RHS (2001): Red-Purple 59-B, 60-B, 61-A, 71-C; the 8-407 line is a representative of this subspecies and is characterized by Purple 77-B with dark center Red-Purple 71-A according to RHS (2001). Representative seeds of OT-8-407 have been deposited under the Budapest Treaty in the Korean Collection for Type Cultures under KCTC 12122BP.

As used herein the term "red" refers to the color range Red 45-A,B,C, 53-C and dark center color according to RHS (2001): Red 46-A, 53-A.

As used herein the term "white" refers to the White 60-N999D according to RHS mini color chart (2005). Representative seeds of OT-7-139 have been deposited under the Budapest Treaty in the Korean Collection for Type Cultures under KCTC 12121BP.

Alternatively or additionally, there is provided a cultivated *Otomeria* plant having flowers characterized by higher (at least 2, 4, 8, 6, 10, 20, 50, 100 folds or higher) Peonidin-hex-deoxyhexose or Malvidin-hex-deoxyhexose values than that found in wild type *Otomeria* oculata.

Alternatively or additionally, there is provided a cultivated *Otomeria* plant having flowers characterized by lower (e.g., 5%, 10%, 20%, 30%, 40%, 50%, 60%, 70%, 80%, 90%, 95%, 99%) Peonidin-hex-deoxyhexose and/or Malvidin-hex-deoxyhexose values than that found in the flower of cultivated *Otomeria* oculata.

Alternatively or additionally, the *Otomeria* plants of some embodiments of the invention are compact, branched and floriferous. Without being bound by theory, it is suggested that novel *Otomeria* plants of some embodiments of the invention have an impaired apical dominance and therefore higher induction of side buds that elongate to longer side stems having flowers at their tips, as compared to wild or cultivated *Otomeria* (e.g., Z-4 and Z-9).

As is further described herein, the present inventors have devised a cultivation approach which resulted in representative plants having some or all of the above described characteristics.

For example, the *Otomeria* plant designated 9-567 (FIG. 4), is characterized by a unique red flower color (RHS Red 46-A, and dark center Red 53-A) and optionally compact and rich-branching habit with continuous flowering.

Representative seeds of OT-9-567 have been deposited under the Budapest Treaty in the Korean Collection for Type Cultures under KCTC 12123BP.

Line 9-567 can be generated by open pollination of a dark-pink colored female parental line with a male parental line. Preferably the female line is 7-85 while the characteristic traits of male parental lines are as follows: red or dark-pink colored flower, compact and branched habit.

Sixteen lines of red flower color have been generated using the present teachings (see FIG. 7). One of these lines was then back-crossed with the 7-85 line to obtain the 9-567 line.

A comparison of line 9-567 to its parental lines demonstrates that this plant exhibits several traits that distinguish it from the parental lines. In particular, 9-567 is characterized by more compact and branched growth habit with abundant flowering. Table 3c below, provides detailed phenotypic description of the 9-567 line.

The *Otomeria* plant designated 8-407 (FIG. 2), is characterized by a unique dark-pink flower color (RHS Purple 77-B with dark center Red Purple 71-A according to RHS 2001) and optionally compact and rich-branching habit with continuous flowering.

Representative seeds of OT-8-407 have been deposited under the Budapest Treaty in the Korean Collection for Type Cultures under KCTC 12122BP.

Line 8-407 can be generated by open pollination of a dark-pink colored female parental line with a male parental line. Preferably the female line is 7-85 while the characteristic traits of male parental lines are as follows: red or dark-pink colored flower, compact and branched habit.

Twelve lines of dark-pink flower color have been generated using these teachings (four of the varieties are illustrated in FIG. 7).

A comparison of line 8-407 to its parental line 8-75, demonstrates that this plant exhibits several traits that distinguish it from the parental lines. In particular, 8-407 is characterized by impaired apical dominance and increased axillary bud outgrowth, which leads to more branched and vigorous growth habit. As a consequence, flowers on the axillary shoots of line 8-407 bloom earlier in comparison to the axillary shoots of line 7-85 which develop later. As a result line 8-407 is more floriferous then its parental line.

Table 3b below, provides detailed phenotypic description of the 8-407.

Figure 1:

The *Otomeria* plant designated 7-62 (Violet 84C with dark center Red-Purple 59-A according to RHS 2001, FIG. 1), representative seeds of which are in the process of deposit under the Budapest Treaty is characterized by a light pink flower color. Further phenotypic description of the line is provided in Table 3c.

Representative seeds of OT-7-62 have been deposited under the Budapest Treaty in the Korean Collection for Type Cultures under KCTC 12120BP.

The 7-62 line can be generated by open pollination of OT-Z-9.

The *Otomeria* plant designated 7-139 (FIG. 3), representative seeds of which have been deposited under the Budapest Treaty in the Korean Collection for Type Cultures under KCTC 12121BP, characterized by a unique white flower color with no detectable dark center (and optionally compact and rich-branching habit with continuous flowering).

Line 7-139 can be generated by open pollination of a cultivated female parental line Z-4 with a male parent. Ten such lines were generated including 7-70; 7-93; 7-129; 7-139; 7-141; 7-154; 7-155; 7-163; 7-164; 7-267 (see FIG. 6).

A comparison of line 7-139 to its parental lines demonstrates that this plant exhibits several traits that distinguish it from the parental lines. In particular, 7-139 is characterized by more compact and branched growth habit with abundant flowering.

An induced polyploid 7-139 was generated according to the present teachings and is distinguishable from the diploid white flowers plant in that it is more compact, shorter, develops more slowly, shorter segments, delayed flowering and has thicker leaves and stems (e.g., about 1.5 fold thicker).

The *Otomeria* line of the present invention can also be subjected to recurrent selection, pedigree breeding and/or backcrossing to generate unique progeny or parental lines most suitable for final progeny production.

Additional screening techniques including restriction fragment length polymorphism selection or genetic marker selection can also be used to further facilitate progeny selection.

Examples 2 of the Examples section which follows describe breeding of *Otomeria* line 9-567.

The *Otomeria* plant designated 8-349 (FIGS. 5a-c, Table 4a), representative seeds of which are in the process of deposit under the Budapest Treaty, has numerous important traits including more intense dark-pink flower color, thicker flower petals and leaves, and a compact and branched habit.

Line 8-349 can be generated by self-pollination of an induced polyploid female parental line and selecting progeny of desired traits. Preferably, the female line is 6-2 (generated by induction of polyploidy in the parent wild-type plant, see Example 3 below). The characteristic traits of this parental line are: induced polyploidy, dark-pink colored flower, compact and non-branching habit.

*Otomeria* line 8-349 of this aspect of the present invention can be generated using breeding and selection techniques as described in the Examples section which follows.

Additional screening techniques including restriction fragment length polymorphism selection (wwwdotncbidotnlmdotnihdotgov/projects/genome/probe/doc/TechR FLPdotshtml) or genetic marker selection (wwwdoteXtensiondotorg/pages/32356/overview-of-traditional-molecular-markers) can also be used to further facilitate progeny selection.

The *Otomeria* line of this aspect of the present invention can also be subjected to recurrent selection, pedigree breeding, transformation and/or backcrossing to generate unique progeny or parental lines most suitable for final progeny production.

Once established, *Otomeria* lines, e.g., 7-139 9-567 or 8-349 can be propagated by using tissue culturing techniques.

As used herein the phrase "tissue culture" refers to plant cells or plant parts from which *Otomeria* plants can be generated, including plant protoplasts, plant cali, plant clumps, and plant cells that are intact in plants, or part of plants, such as seeds, leaves, stems, pollens, roots, root tips, anthers, ovules, petals, flowers and embryos.

Techniques of generating plant tissue culture and regenerating plants from tissue culture are well known in the art. For example, such techniques are set forth by Vasil (1984) [Cell Culture and Somatic Cell Genetics of Plants, Vol I, II, III Laboratory Procedures and Their Applications Academic Press, New York]; Green et al. (1987) [Plant Tissue and Cell Culture, Academic Press, New York]; Weissbach and Weissbach (1989) [Methods for Plant Molecular Biology, Academic Press]; Gelvin et al. (1990) [Plant Molecular Biology Manual, Kluwer Academic Publishers]; Evans et al. (1983) [Handbook of Plant Cell Culture, MacMillian Publishing Company, New York]; and Klee et al. (1987) [Ann. Rev. of Plant Phys. 38:467-486].

*Otomeria* of the present invention can be genetically transformed using methods which are well known in the art. According to other embodiments, the *Otomeria* of the present invention is a naïve plant which is not genetically modified.

Vegetative portions of the plants of the invention can be planted. Thus the present invention also contemplates a planted field or a potted plant.

Thus embodiments of the invention provide for *Otomeria* plants having commercially valuable traits such as compact and branched habit, floriferous and continuous flowering, high tolerance to heat (can thrive in temperatures of 26° C. or above) and/or in full sunlight or partial shade.

Embodiments of this aspect of the present invention also relate to a seed of the *Otomeria* plant; a tissue culture of regenerable cells of the *Otomeria* plant; a tissue culture regenerating plants capable of expressing all the morphological and physiological characteristics of the *Otomeria* plant; and a tissue culture regenerated from cells or protoplasts of a tissue selected from the group consisting of seeds, leaves, stems, pollens, roots, root tips, anthers, ovules, petals, flowers and embryos.

The present invention also relates to an *Otomeria* plant derived from any of the *Otomeria* plants described herein, or their parts.

According to another aspect of the present invention there is provided a method of developing an *Otomeria* plant using plant breeding techniques which employ an induced polyploid *Otomeria* plant having a higher chromosome number than that found in *Otomeria oculata* as a source of plant breeding material.

The method of this aspect of the present invention further relates to plant breeding techniques selected from the group consisting of recurrent selection, backcrossing and pedigree breeding.

The present invention successfully addresses the shortcomings of the presently known configurations by providing *Otomeria* plants characterized by a combination of highly desirable commercial traits and by providing methods and systems for generating same.

Thus, this aspect of the present invention provides novel *Otomeria* plants, seeds and tissue culture for generating same. This aspect of the present invention further provides a system for developing such an *Otomeria* plant which system includes *Otomeria* plants or parts of thereof as a source of the breeding material.

The *Otomeria* plants disclosed herein have certain morphological and growth traits such as compact and branched habit and new flower colors (e.g. pure white, pink, dark pink and red) which differ from prior art *Otomeria* plants; these traits render the present varieties both economically and agronomically valuable.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cultivation of *Otomeria oculata* Plants

Seeds of plants growing in the wild (deposited under the Budapest Treaty in the Kew Gardens Herbarium and described by each of wwwdotappsdotkewdotorg/herbcat/getHomePageResults.do?homePageSearchText=OTOMERIA+OCULATA&homePageSearchOption=scientific_name&nameOfSearchPage=home_page&x7&y=4.

Flora of Tropical East Africa, page 1 (1976) Author: B. Verdcour citing the work of S. Moor) were germinated into plants which were botanically identified as the species *Otomeria oculata*. Seeds of these plants were grown and used in breeding the novel *Otomeria* varieties of some embodiments of the present invention.

Materials and Methods

Female parent lines were not emasculated but were pollinated by bees and other insects. Ripening of the seeds occurs 2-3 months after pollination, depending on the environmental conditions. Collected seeds of *Otomeria* were sown and after two weeks, seedlings were transferred to trays of peat under mist. After a month, plants were planted in 12 cm pots with peat based potting mix or planted in a field flowerbed, for observations and selections. Rooting took 14-18 days at temperatures of 68-75° F. (20-24° C.), preferably in jiffy. Planting of the rooted cuttings was done in 5" (12 cm) pots, at one plant per pot, in 6" (15 cm) pots at 1-2 plants per pot or in a 10" (25 cm) pot, at 3-4 plants per pot.

Light intensity conditions optimal for growing of cultivated *Otomeria* are full sunlight to partial shade (min6000 FC/60,000 LUX). High light intensities are best for compact habit growth and rich-flowering plants. Shading up to 40% is also possible, but a second pinch or growth regulators might be needed. Heavier shade would cause stretching and poor flowering.

*Otomeria* is a heat-loving plant. At temperatures of 86° F. (30° C.) and even above—the plants thrive. On the other hand, when temperatures drop below 59° F. (15° C.)—growth stops and below 50° F. (10° C.) the plants show chilling injuries.

Asexually propagation of cultivated *Otomeria* plants is made by cuttings from young shoots, including at least one vegetative branch or meristem.

Results

The plants grown from the wild *Otomeria* seeds matured to an erect subshrubby herb. Table 1 below lists typical characteristic traits of these plants.

TABLE 1 phenotypic traits *Otomeria oculata* (described by S. Moor)

| | |
|---|---|
| height | 0.5-0.8 m |
| stems | Shortly adpressed, hairy |
| Leaf blades | lanceolate or narrowly rhomboid, 2.5-6.5(-8.5) cm. long, 0.7-2.3 cm. wide, more or less acute at the apex, narrowly cuneate at the base, shortly hairy above and with longer adpressed bristly hairs beneath |
| Petioles | obsolete or up to 8 mm long |
| Stipules | 1-3 flat segments 1.5-3 mm long |
| Inflorescence | Initially capitate, transition to a spike 5-32 cm long, with flowers widely spaced at the base; peduncles 4.5-10 cm long; flowers dimorphic |
| Calyx-tube | Green to red 1-2 mm. long, glabrous or bristly; larger lobes linear, 0.5-1.5 cm long, 0.5-1.3 mm wide. |
| Corolla-tube | white, reddish or pink, 1.8-3.2 cm. long, dilated at the apex in long-styled flowers to 1.2-2.25 mm. for a distance of 4-5.5 mm (corolla-tube in short-styled flowers gradually widened at the apex) |
| Corolla-lobes | Light Pink and pink with a crimson pubescent eye, broadly elliptic, 0.5-1 cm. long, and 2-5.5 mm wide (thrum flower) or 6-10 mm. wide (pin flower) |
| Fruit | obtriangular-oblong, ribbed, 3.5-6 mm. long, 2.5-4.5 mm. wide, pubescent |

Among the population grown were tall plants, 70-80 cm, with long and poor flowering spikes and light-pink pin flowers. These wild plants were unacceptable for horticultural purpose because they were tall, with a poor growing habit. Moreover, the color range of the flowers was limited to two tones of pink. Other types of plants were shorter, with small, pink thrum flowers.

Plants of the source population were found to be fertile when directly crossed with each other in open and self-pollinations. These crosses resulted in hundreds of seeds, which were sown and then planted in the field for observation.

Forty resulting lines having flowers of pink color variations, high or compact habit, medium or large flower and rich-branching habit were selected for further breeding. Specifically, *Otomeria* lines selected for further breeding were characterized by the following traits: woody shrublet 30-50 cm tall, with opposite elliptic leaves, light green in color. The flower is salver form—the corolla has a narrow (1-3 mm), long (25-30 mm) tube, which abruptly expands to five (sometimes six) petals, fused at their bases. Flower petal shapes are diverse—oblong, elliptic, orbicular or obovate, with acute, abruptly acute or obtuse tips. Flower's corolla is 15-36 mm long and the petals are 7.5-18 mm long. The flower tube is 25-30 mm long.

Example 2

Production of *Otomeria* Cultivars Having White, Red or Dark Pink Flowers

Two lines of cultivated *Otomeria* (generated as described in Example 1) were selected for further breeding as they exhibited horticultural favorable traits i.e., Z-4 and Z-9, RHS-Red-purple 69D and Purple 76-C, respectively. Z-4 and Z-9 are habit similar, the Z-4 cultivar is a bit higher than the Z-9. The flowers for Z-4 are larger and brighter as compared to the Z-9.

Open pollination was utilized in order to improve seed yield over controlled crosses and breeding was repeated over a period of five years with selections for the following desired traits: flower color range (see Table 2 below), different growth habits; compact/up-right/ball shaped/rich branching/rich-flowering, short-pedicels branches, compressed flowering spikes, different flower shapes, flower size, number of petals, dark foliage, early flowering etc., In addition, *Otomeria* plants characterized by tall and strong branches were also selected for the cut flower breeding program.

TABLE 2

Flower color selection of bred *Otomeria* lines

Flower color segregation of the selected lines

| RED | WHITE (pure) | DARK PINK | PINK | LIGHT PINK | Selected lines | Population size |
|---|---|---|---|---|---|---|
| — | — | — | — | — | 10 | few seeds |
| — | — | — | 17 | 23 | 40 | 700 |
| — | 10 | 1 | 135 | 92 | 238 | 5,000 |
| 16 | 26 | 12 | 45 | 17 | 125 | 5,000 |
| 26 | 7 | 59 | 104 | 113 | 309 | 5,000 |

The 7-85 line generated by open or self-pollination on Z-9 line exhibits a dark pink flower. In order to increase the occurrence of new flower color tones, 7-85 was used as the female parent in open field pollinations resulting in a population of 1,100 plants. Twelve dark-pink lines and sixteen red lines were selected. The breeding is described in FIG. 7 right side. The dark-pink lines included e.g., OT-8-361, OT-8-369, OT-8-381, OT-8-387.

One of the lines generated by open pollination of OT-7-85 and exhibited superior horticultural traits was designated 8-407 (RHS: Purple 77-B with a dark center Red purple 71-A). The red flowered *Otomeria* lines listed in FIG. 7 (e.g., designated as 8-300-8-311; 8-336-8-338; 8-340, Red 46-A, 53-A) represent the first known *Otomeria* with such flower color. In order to improve the growth habit of the red colored lines, red lines (8-300; 8-304; 8-306; 8-311) and dark pink lines (8-361, 8-369, 8-381, 8-387) selected for compact and rich-branching habit were backcrossed and hybridized with 7-85. One resulting line of red colored flower and improved growth habit was selected and designated 9-567 (FIG. 4).

Figure 4:

TABLE 3a traits of *Otomeria* line 9-567 (FIG. 4)

| | |
|---|---|
| height | 0.3 m |
| stems | Shortly adpressed, hairy |
| Leaf blades | ovate, 6 cm. long, 2.5 cm. wide, acute at the apex, narrowly cuneate at the base, shortly hairy above and with longer adpressed bristly hairs beneath |
| Petioles | up to 10 mm long |
| Stipules | 1-3 flat segments 2 mm long |
| Inflorescence | Initially capitate, transition to a spike 14 cm long, with flowers widely spaced at the base; peduncles 4 cm long |
| Calyx-tube | Brown, 2 mm. long, bristly; larger lobes linear, 1 cm long, 0.5 mm wide. |
| Corolla-tube | Red, 2.5 cm. long, dilated at the apex to 3 mm for a distance of 3 mm |
| Corolla lobes | Red with a dark Red pubescent eye, elliptic, 1 cm. long, 8 mm. wide |
| RHS | Red 46-A, with a dark center 53-A |
| Fruit | Conical, 3 mm. long, 2 mm. wide, pubescent |

Figure 2:
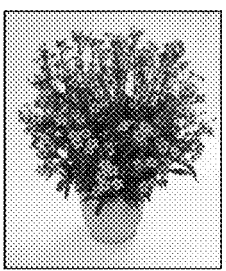

TABLE 3b traits of *Otomeria* line 8-407 (FIG. 2)

| | |
|---|---|
| height | 0.4 m |
| stems | Shortly adpressed, hairy |
| Leaf blades | ovate, 6.5 cm. long, 2.5 cm. wide, acute at the apex, narrowly cuneate at the base, shortly hairy above and with longer adpressed bristly hairs beneath |
| Petioles | up to 10 mm long |
| Stipules | 1-3 flat segments 2 mm long |
| Inflorescence | Initially capitate, transition to a spike 20 cm long, with flowers widely spaced at the base; peduncles 5 cm long; |
| Calyx-tube | Brown, 2 mm. long, bristly; larger lobes linear, 1 cm long, 1 mm wide. |
| Corolla-tube | Dark Pink, 3 cm. long, dilated at the apex to 3 mm for a distance of 3 mm |
| Corolla Lobes | Dark Pink with a Purple pubescent eye, elliptic, 1 cm. long, 8 mm. wide |
| RHS | Purple 77 B with a dark center Red Purple 71-A |
| Fruit | Conical, 3 mm. long, 2 mm. wide, pubescent |

TABLE 3c traits of *Otomeria* line 7-62 (FIG. 1)

| | |
|---|---|
| height | 0.35 m |
| stems | Shortly adpressed, hairy |
| Leaf blades | ovate, 6 cm. long, 2 cm. wide, acute at the apex, narrowly cuneate at the base, shortly hairy above and with longer adpressed bristly hairs beneath |
| Petioles | up to 6 mm long |
| Stipules | 1-3 flat segments 2 mm long |

TABLE 3c-continued traits of *Otomeria* line 7-62 (FIG. 1)

| | |
|---|---|
| Inflorescence | Initially capitate, transition to a spike 15 cm long, with flowers widely spaced at the base; peduncles 4 cm long; |
| Calyx-tube | Brown, 2 mm. long, bristly; larger lobes linear, 1 cm long, 1 mm wide. |
| Corolla-tube | Light Pink, 2.5 cm. long, dilated at the apex to 3 mm for a distance of 3 mm |
| Corolla Lobes | Light Pink with a Purple pubescent eye, elliptic, 1 cm. long, 9 mm. wide |
| RHS | Violet 84-C with a dark center Red Purple 59-A |
| Fruit | Conical, 3 mm. long, 2 mm. wide, pubescent |

Open and self-pollination of Z-4 line was utilized and 10 resulting lines of white colored flower were selected and designated: 7-70; 7-93; 7-129; 7-139; 7-141; 7-154; 7-155; 7-163; 7-164; 7-267. The outline of this breeding program is shown in the flow chart of FIG. 6.

Figure 3:
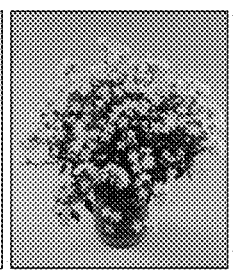

TABLE 3d traits of *Otomeria* line 7-139 (FIG. 3, FIG. 6, non-multiplied)

| | |
|---|---|
| height | 0.3 m |
| stems | Shortly adpressed, hairy |
| Leaf blades | Ovate, 5 cm. long, 2 cm. wide, acute at the apex, narrowly cuneate at the base, shortly hairy above and with longer adpressed bristly hairs beneath |
| Petioles | up to 8 mm long |
| Stipules | 1-3 flat segments 3 mm long |
| Inflorescence | Initially capitate, transition to a spike 8 cm long, with flowers widely spaced at the base; peduncles 2 cm long; |
| Calyx-tube | Green, 2 mm. long, bristly; larger lobes linear, 0.9 cm long, 0.5 mm wide. |
| Corolla-tube | Light Green, 2 cm. long, dilated at the apex to 2 mm for a distance of 5 mm |
| Corolla Lobes | White with a White pubescent eye, elliptic, 1.1 cm. long, 8 mm. wide |
| RHS | White 60-N999D |
| Fruit | Conical, 2 mm. long, 2 mm. wide, pubescent |

Example 3

In Vitro Induction of Polyploidy in *Otomeria oculata*

The manipulation of ploidy in plant tissue has been used to introduce fertility into hybrids and to produce plants with improved horticultural or agronomic traits. Phenotypic changes due to ploidy increase in flowering plants are often larger blooms, more intense color, thicker leaves, robust stems, or they may have thicker flower petals that last longer than their diploid counter-parts (Kehr, A. E. 1996. *Woody plant polyploidy. American Nurseryman.* 183:38-47).

There is no information in the literature regarding induction of ploidy in *Otomeria* species. Nonetheless, in order to breed a cultivated *Otomeria* plant with improved horticulture traits, the present inventor employed an approach for treating cultured *Otomeria*'s explants with the antimitotic herbicide Oryzalin.

Materials and Methods

Internodal segments of cultivated *Otomeria oculata* (2 to 4 cm long) designated Z-9 were cultured in half strength Murashige and Skoog (MS) basal medium supplemented with 3% sucrose and 1% agar. Medium was sterilized by autoclave (121° C. for 20 min) and then supplemented with growth regulators for shoot multiplication (Gibberellin and benzylaminopurine). Oryzalin aqueous solution was added at final concentration of 0.05 mM to 0.5 mM, with 0.25% v/v Dimethyl sulfoxide (DMSO). Cultures were incubated at 23±2° C. under a 16 h photoperiod. Segments were re-cut after 2 weeks and placed into fresh half strength MS basal medium. After 2-3 weeks, regenerated shoots were cut and placed into MS basal solid medium for rooting, before subsequently being transferred to a greenhouse for acclimatization. Oryzalin concentrations higher than 0.4 mM resulted in chemical toxicity as observed by a decrease in the survival of nodal cultures and a significant decrease in rooting of the treated plantlets. The effect of oryzalin concentration on chromosome doubling of *Otomeria*'s varieties was also studied. Survival and regeneration rates were determined and ploidy level of regenerated plantlets was evaluated by flow cytometry (Plant Cytometry Services—Schijndel, Netherlands) for all oryzalin treatments compared to un-treated varieties.

Results

The outline of this approach is shown in the flow chart of FIG. 7 left side. Oryzalin treatment of *Otomeria* Z-9 (RHS-Purple 76C) resulted in generation of several polyploidy lines including compact plants (30-35 cm) with dark-pink flowers (designated as "6-2"). Self-pollination of 6-2 resulted in the generation tens of progenies, of which 18 lines were selected for the following desired traits: more compact and branched appearance with rich flowering. The breeding program was continued using the polyploidy line 8-349 (FIG. 5, Table 4a) which is characterized by more intense flower color (Purple 76-B), compact and branched habit and thicker foliage.

In addition, the present inventor has induced polyploidy in white *Otomeria* plants as follows (see flow chart of FIG. 6). The breeding program was continued using the white line 7-139 (FIG. 3, table 3d) which is characterized by ball-shaped, compact habit and rich-flowering with compressed flowering spikes. 7-139 was also treated with oryzalin in order to induce chromosome duplication and breed hardier *Otomeria* plants. Explants of line 7-139 were treated on solid medium with oryzalin at final concentration of 0.15 mM to 0.5 mM. After 7-14 days the treated explants were transferred into new medium for regeneration. Shoot regenerates were later rooted on rooting medium, before being moved to hardening in the greenhouse. Polyploid nuclei of oryzalin-treated plant were determined via flow cytometry and compared to an un-treated 7-139 line. The results indicated that 0.20 mM to 0.35 mM Oryzalin treatments were effective for producing polyploidy plants of line 7-139. The polyploidy lines were characterized by white colored flower with thick petals, compact ball-shaped habit with thick foliage. Thickness of petals and foliage gave the plant a hardier appearance. The polyploidy lines were integrated into the breeding programs in order to transfer these phenotypic traits into different genetic backgrounds.

The breeding program resulted in stable lines which represent new *Otomeria* varieties.

TABLE 4a traits of *Otomeria* line 8-349 (FIG. 5)

| | |
|---|---|
| height | 0.25 m |
| stems | Shortly adpressed, hairy and thick - about 4 mm |
| Leaf blades | Ovate, 4 cm. long, 1.5 cm. wide, acute at the apex, narrowly cuneate at the base, shortly hairy above and with longer adpressed bristly hairs beneath |
| Petioles | up to 5 mm long |
| Stipules | 1-3 flat segments 1 mm long |

TABLE 4a-continued traits of *Otomeria* line 8-349 (FIG. 5)

| | |
|---|---|
| Inflorescence | Initially capitate, transition to a spike 12 cm long, with flowers widely spaced at the base; peduncles 3 cm long; |
| Calyx-tube | Brown, 2 mm. long, bristly; larger lobes linear, 1 cm long, 0.5 mm wide. |
| Corolla-tube | Pink, 2 cm. long, dilated at the apex to 3 mm for a distance of 5 mm |
| Corolla Lobes | Dark Pink with a Purple pubescent eye, elliptic, 1 cm. long, 7 mm. wide |
| RHS | Purple 76-C |
| Fruit | Conical, 2 mm. long, 3 mm. wide, pubescent |

TABLE 4b ploidy of some *Otomeria* cultivars generated using the present approach

| Species | SAMP. | Ref. | Ploidy | DNA ratio | line |
|---|---|---|---|---|---|
| Otomeria | PN-1 | PN-1 | 2x | 1.65 | OT-Z-4 |
| Otomeria | PN-2 | PN-1 | 2x | 1.69 | OT-Z-9 |
| Otomeria | PN-3 | PN-1 | 4x | 3.26 | OT-6-2 |
| Otomeria | PN-4 | PN-1 | 2x | 1.67 | OT-7-62 |
| Otomeria | PN-5 | PN-1 | 2x | 1.65 | OT-7-139 |
| Otomeria | PN-6 | PN-1 | 2x | 1.67 | OT-8-407 |
| Otomeria | PN-7 | PN-1 | 2x | 1.68 | OT-9-567 |
| Otomeria | PN-8 | PN-1 | 2x | 1.66 | OT-7-85 |
| Otomeria | PN-9 | PN-1 | 4x | | OT-9-431 |
| Otomeria | PN-10 | PN-1 | 4x | 3.27 | OT-9-432 |
| Otomeria | PN-11 | PN-1 | 4x | | OT-8-349 |

Example 4

Pigment Analysis in Cultivated and Novel *Otomeria* Plants

Flowers from a number of *Otomeria* plants generated according to the present teachings were subjected to pigment analysis.

Materials and Methods

Anthocyanins Determination by UPLC-QTOF-MS 150 mg of frozen fine powder of *Otomeria* petals were extracted by 70% methanol and 2% formic acid in a ratio of 1:4 w/v (tissue:extraction solution) followed by 20 min incubation in a bath sonicator and centrifugation 10 min at 13000 rpm. The supernatant was filtered through 0.22 μn PTFE membrane filter (Acrodisc® CR 13 mm; PALL) before injection to UPLC-QTOF-MS instrument.

Mass spectral analysis of semi-polar compounds was carried out with an UPLC-QTOF instrument (Waters HDMS Synapt), with the UPLC column connected online to a PDA detector (190-500nm) and then to the MS detector as previously described (Mintz-Oron et al., 2008 Gene expression and metabolism in tomato fruit surface tissues. Plant Physiol 147, 823-851.). Separation of metabolites was performed by gradient elution (acetonitrile-water, containing 0.1% formic acid) on a 100×2.1-mm i.d., 1.7-μm UPLC BEH C18 column (Waters Acquity). Masses of the eluted compounds (m/z range from 50 to 1500 Da) were detected with a QTOF-MS equipped with an ESI source (performed in both positive and negative modes), at 4 eV collision energy. MSMS spectra for compounds identification were acquired at collision energies 10 eV, 25 eV and 35 eV at positive ionization mode. The UV spectra (200-650 nm) were acquired on a UPLC-MS (Waters Xevo TQ MS) instrument with the UPLC column connected online to a PDA detector (Acquity 2996 PDA) and then to the MS detector. The UPLC column and LC conditions were the same as for the UPLC-QTOF analysis. Compounds were putatively identified by comparison of the observed UV, MS/MS spectra and determined elemental composition with those found in the literature.

Results

The results of pigment analysis are presented in Tables 5A-C below and summarized in FIG. 8.

TABLE 5a

Compound 1: Peonidin-hex-deoxyhexose

| | | Area | | | | STDEV |
| --- | --- | --- | --- | --- | --- | --- |
| | RT | rep. 1 | rep. 2 | rep. 3 | rep. 4 | AVERAGE | Peonidin |
| OT-7-139 | | ND | ND | ND | ND | ND | 0 |
| OT-7-62 | 7.31 | 139.192 | 82.232 | 61.891 | 81.239 | 91.14 | 33.376 |
| OT-8-407 | 7.34 | 208.382 | 237.225 | 271.512 | 176.775 | 223.47 | 40.436 |
| OT-9-567 | 7.31 | 8166.087 | 7448.107 | 6821.704 | 6101.735 | 7134.41 | 880.712 |
| OT-Z-4 | 7.39 | 19.902 | 16.727 | 9.66 | 14.276 | 15.14 | 4.319 |
| OT-Z-9 | 7.36 | 65.532 | 55.496 | 58.611 | 46.637 | 56.57 | 7.837 |
| OT-7-85 | 7.34 | 223.059 | 168.334 | 118.577 | 145.233 | 163.80 | 44.429 |
| OT-8-349 | 7.37 | 93.33 | 121.167 | 57.967 | 68.387 | 85.21 | 28.190 |

TABLE 5b

Compound 2: Malvidin-hex-deoxyhexose

| | | Area | | | | STDEV |
| --- | --- | --- | --- | --- | --- | --- |
| | RT | rep. 1 | rep. 2 | rep. 3 | rep. 4 | AVERAGE | Malvidin |
| OT-7-139 | 8.1 | 28.524 | 20.049 | 24.009 | 17.927 | 22.63 | 4.669 |
| OT-7-62 | 7.55 | 1787.999 | 1242.95 | 1088.427 | 1230.568 | 1337.49 | 308.415 |
| OT-8-407 | 7.52 | 2356.371 | 2356.913 | 2450.203 | 1868.91 | 2258.10 | 263.181 |
| OT-9-567 | 7.6 | 6876.835 | 6464.319 | 5198.954 | 4376.707 | 5729.20 | 1150.052 |
| OT-Z-4 | 7.58 | 605.61 | 469.362 | 437.806 | 398.66 | 477.86 | 89.943 |
| OT-Z-9 | 7.54 | 1201.699 | 1100.236 | 1036.338 | 891.933 | 1057.55 | 129.717 |
| OT-7-85 | 7.54 | 2909.394 | 2288.674 | 1954.735 | 2013.371 | 2291.54 | 436.870 |
| OT-8-349 | 7.57 | 1679.961 | 1802.444 | 1128.059 | 1240.624 | 1462.77 | 328.598 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. An Otomeria plant of line (OT-8-407) for which representative seeds have been deposited under the Budapest Treaty in the Korean Collection for Type Cultures under KCTC 12122BP.

2. An Otomeria plant of line (OT-7-62) for which representative seeds have been deposited under the Budapest Treaty in the Korean Collection for Type Cultures under KCTC 12120BP.

3. An Otomeria plant of line (OT-9-567) for which representative seeds have been deposited under the Budapest Treaty in the Korean Collection for Type Cultures under KCTC 12123BP.

4. An Otomeria plant of line (OT-7-139) for which representative seeds have been deposited under the Budapest Treaty in the Korean Collection for Type Cultures under KCTC 12121BP.

* * * * *